(12) United States Patent
Parida et al.

(10) Patent No.: US 9,035,086 B2
(45) Date of Patent: May 19, 2015

(54) MODIFIED LAYERED DOUBLE HYDROXIDE (LDH) AND A PROCESS FOR PREPARATION THEREOF FOR C—C BOND FORMING REACTIONS

(75) Inventors: Kulamani Parida, Orissa (IN); Sudarshan Singha, Orissa (IN); Mitarani Sahoo, Orissa (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 729 days.

(21) Appl. No.: 13/396,022

(22) Filed: Feb. 14, 2012

(65) Prior Publication Data

US 2012/0209023 A1 Aug. 16, 2012

(30) Foreign Application Priority Data

Feb. 14, 2011 (IN) .............................. 365/DEL/2011

(51) Int. Cl.
| | | |
|---|---|---|
| B01J 27/24 | (2006.01) | |
| C07C 211/03 | (2006.01) | |
| B01J 21/00 | (2006.01) | |
| C07C 67/00 | (2006.01) | |
| B01J 37/00 | (2006.01) | |
| B01J 37/08 | (2006.01) | |
| C07C 253/30 | (2006.01) | |
| C07C 201/12 | (2006.01) | |
| B01J 23/00 | (2006.01) | |
| B01J 35/00 | (2006.01) | |
| C07C 67/347 | (2006.01) | |
| C07B 37/02 | (2006.01) | |
| C07B 37/04 | (2006.01) | |
| C07C 45/72 | (2006.01) | |
| B01J 23/06 | (2006.01) | |

(52) U.S. Cl.
CPC .............. *C07C 253/30* (2013.01); *C07C 201/12* (2013.01); *B01J 23/007* (2013.01); *B01J 23/06* (2013.01); *B01J 35/002* (2013.01); *C07C 67/347* (2013.01); *C07B 37/02* (2013.01); *C07B 37/04* (2013.01); *C07C 45/72* (2013.01)

(58) Field of Classification Search
CPC ............................. B01J 23/007; C07C 211/03
See application file for complete search history.

(56) References Cited

PUBLICATIONS

Choi et al. "Monolayer Assembly of Zeolite Crystals on Glass with Fullerene as the Covalent Linker" Journal of the American Chemical Society, 2000, vol. 122, pp. 5201-5209.*

* cited by examiner

*Primary Examiner* — Joseph Kosack
(74) *Attorney, Agent, or Firm* — Ladas & Parry LLP

(57) ABSTRACT

The present invention relates to a covalently organo-modified LDH (LDH/APTES) was found to be an efficient and reusable heterogeneous catalyst for C—C bond forming reactions (i.e. Aldol condensation, Knoevenagel condensation, Henry reaction, Michael addition). More particularly, this catalyst shows consistent activity for several cycles in C—C bond forming reaction. These catalysts were successfully characterized by XRD, FT-IR, $^{29}$Si CP MAS NMR.

17 Claims, 3 Drawing Sheets

Catalyst Characterisation:

MODIFIED LAYERED DOUBLE HYDROXIDE (LDH) AND A PROCESS FOR PREPARATION THEREOF FOR C—C BOND FORMING REACTIONS

FIELD OF INVENTION

The present invention relates to a modified layered double hydroxide. The presents invention also relates to a process for the preparation of layered double hydroxide (LDH) modified with an organic moiety, which is useful in base catalyzed reactions at room temperature.

The present invention particularly relates to modification of LDH by a covalent linking agent such as an aminopropyl triethoxysilane (APTES), a novel and reusable catalyst for base catalyzed reactions.

BACKGROUND OF THE INVENTION

Inorganic-organic hybrid materials obtained by introducing an organic group in between the layers/voids of inorganic layered materials have the potential to demonstrate the characteristics that cannot be achieved by an individual host or guest. Grafting reactions occur by establishing covalent bonds between the reactive groups of the layer and an adequate reactant molecule, which ensures greater chemical, structural, and thermal stability for the compound. Recently, many examples of surface modified silica, glasses and zeolite-like porous materials involving covalent bond formation with organo silanes have been widely investigated. [A. Kulak, Y. J. Lee, Y. S. Park, K. B. Yoon, Angew. Chem. Int. Ed. 5 (2000) 950; K. C. Vrancken, L. De Coster, P. Van Der Voort, P. J. Grobet, E. I. Vansant, J. Colloid. Interface Sci. 170 (1995) 71; S. Y. Choi, Y. J. Lee, Y. S. Park, K. Ha, K. B. Yoon, J. Am. Chem. Soc. 122 (2000) 5201]. LDH is ubiquitous, economical and non-toxic powder having a high anion exchange capacity, good adsorbent, swelling, and intercalation properties. These profitable features of anionic clay make it useful in the move towards establishing environmental friendly catalyst [B. M. Chaudhary, M. L. Kantam, V. Neeraj, K. K. Rao, F. Figureras, L. Delotte, Green Chem. 3 (2001) 257]. Due to the above exiting properties different anionic surfactant, metal complexes and enzymes have been incorporated via an electrostatic force of attraction [S. Bhattacharjee, J. A. Anderson Chem. Commun., (2004) 554.; E. Gardner, T. J. Pinnavaia, Appl. Catal., 167 (1998) 65; B. M. Choudary, S. Madhi, N. S. Chowdari, M. L. Kantam, B. Sreedhar, J. Am. Chem. Soc. 124 (2002) 14127; S. Bhattacharjee and J. A. Anderson, Catalysis Letters. 95 (2004) 119; S. Gago, M. Pillinger, A. A. Valente, T. M. Santos, J. Rocha, and I. S. Goncalves, Inorg. Chem. 43 (2004) 5422]. But till date studies on covalent attachment of organic moieties (APTES) in LDH, which can enhance the catalytic activity of LDH have never been explored.

This invention particularly relates to an eco-friendly process employing recyclable LDH-APTES as a heterogeneous catalyst in place of soluble bases for Aldol condensation, Knoevenagel condensation, Henry reaction and Michael addition. This present invention provides an interlayer surface modified LDH with organic moieties through covalent bonding. This technique involves the insertion of long chain anionic surfactant into LDH host, which offers a gentle way of expanding the interlayer space of LDH. That will make the layered material more compatible with the intercalated organic moiety.

Reference may be made to US patent U.S. Pat. No. 4,458, 026 wherein aldol condensation of acetone is carried out by heat-treated synthetic anionic clay. The inherent disadvantage in this process is higher temperatures and longer reaction time with lower yields. Reference may be made to Choudary et al., Tetrahedron, 56 (2000) 9357 wherein Knoevenagel condensation and Michael addition is carried out by Mg—Al—O-t-Bu hydrotalcite. The inherent disadvantage in this process is the catalyst is more sensitive to moisture. Reference may be made to Choudary et al., Green. Chem., (1999) 187 wherein Henry reaction is carried out by Mg—Al rehydrated hydrotalcite. The inherent disadvantages in the process are low yields, longer reaction time and require activation for each catalytic cycle to reuse. Hence to avoid these above problems, we demonstrate for the first time a process that provides an innovative mean of consistent activity for several cycles in C—C bond forming reactions at room temperature. This makes the process economical and possible for commercial realisation. Therefore, LDH/APTES is better alternative for of base catalyze reactions. Thus this invention offers the best techno-economic route for the synthesis of intermediates in the preparation of drugs, pharmaceuticals and fine chemicals.

DEFINITIONS

LDH: LAYERED DOUBLE HYDROXIDE
Room Temperature: Temperature in the range of 20° C.-35° C.
APTES: Aminopropyl triethoxysilane
CTAB: Cetyl trimethylammonium bromide
SDS: Sodium Dodecyl Sulfate

OBJECTS OF THE INVENTION

The main objective of the present invention is to provide a modified layered double hydroxide (LDH) for base catalyzed reactions.

Another objective of the present invention is to provide a process for preparation of an interlayer surface modified layered double hydroxide (LDH) by organic moiety (APTES) for base catalyzed reactions which obviates the drawbacks of the hitherto known prior art as detailed above.

Further objective of the present invention provides a new approach that furnishes an appealing pathway to prepare LDH/APTES through simple exchange process in which APTES is covalently bonded with interlayer surface of LDH which is a better alternative for various base catalyzed reactions resulting a high yield.

Still another objective of the present invention is to provide use of heterogeneous recyclable LDH/APTES for C—C bond forming reactions comprising Aldol, Knoevenagel, Henry and Michael by simple filtration and reuse for number of cycles with consistent activity under mild conditions.

SUMMARY OF THE INVENTION

Accordingly the present invention provides a modified layered double hydroxide (LDH) catalyst wherein the catalyst comprising: $Zn(OH)_2$, $Al(OH)_3$ and APTES ranging between 76-70%, 21-24% and 3-6%, respectively wherein the basal spacing ($d_{003}$) peak at 23.2 Å and Al—O and Zn—O lattice vibrations is around 445 and 675 $cm^{-1}$ in LDH.

In an embodiment of the invention wherein the modified layered double hydroxide (LDH) is useful as catalyst for C—C bond forming reactions.

In another embodiment of the invention wherein the C—C bond forming reactions is selected from a group consisting of aldol/α,β-unsaturated ester/β-nitroalkanols/Michael addition product.

In yet another embodiment of the invention wherein the reaction may be performed using the catalyst at room temperature.

In another embodiment of the invention wherein the reaction is performed for a period of 0.5 to 48 h in the presence of the modified layered double hydroxide (LDH).

In yet another embodiment of the invention wherein the yield of the products obtained is ranging between 80-98%.

Accordingly, the present invention also provides a process for preparation of modified layered double hydroxide wherein the process comprising the steps of:

(a) preparing a mixed solution of $Zn(NO_3)_2.6H_2O$ and $Al(NO_3).9H_2O$ in water in the ratio ranging between 4:1 to 2:1 respectively at a pH of 10 by addition of NaOH,
(b) adding slowly the mixed solution of step (a) to an anionic solution of sodium dodecyl sulfate (SDS) in water,
(c) adding NaOH solution to the above said mixture of step (b) to maintain pH of the whole solution at 7 to obtain a slurry;
(d) aging the slurry obtained in step (c) hrs,
(e) filtering the product thus obtained in step (d) and washing with water, followed by drying to obtain LDH precursor containing SDS,
(f) adding aminopropyl triethoxysilane (APTES) to the LDH precursor containing SDS of step (e) followed by addition of cetyl trimethylammonium bromide (CTAS) in a solvent and kept/set aside the whole mixture for reaction,
(g) washing product thus obtained in step (f), filtering and drying to obtain the modified layered double hydroxide (LDH).

In an embodiment of the invention wherein the ratio of Zn:Al:SDS in step (b) is in the range of 4:1:2 to 2:1:4, respectively.

In another embodiment of the invention wherein ratio of $Zn(NO_3)_2:Al(NO_3)_3:SDS:CTAB:APTES$ is in the range of 4:1:2:48.48:6.424 to 2:1:4:80:12.

In yet another embodiment of the invention wherein the slurry in step (d) is aged for 45-48 hrs.

In another embodiment of the invention wherein the slurry in step (d) is aged at a temperature in the range of 65° C. to 70° C.

In yet another embodiment of the invention wherein washing of the product in step (g) is done with dichloromethane.

In still another embodiment of the invention wherein drying in step (g) is carried out at a temperature range of 20° C.-35° C.

In another embodiment of the invention wherein the whole reaction mixture in step (f) is reacted for 40-48 hrs.

In yet another embodiment of the invention, wherein the whole reaction mixture in step (f) is reacted at a temperature in the range of 20-35° C.

In yet another embodiment of the invention wherein cetyl trimethylammonium bromide (CTAB) used is in the ratio of Zn:Al:CTAB in the range of 4:1:48.48 to 2:1:80 respectively.

In still another embodiment of the invention wherein the solvent used in step (f) is selected from group consisting of dichloromethylene, chloroform, ethanol, and methanol.

DETAILED DESCRIPTION OF THE INVENTION

Synthesis of ZnAl-LDH/SDS via co-precipitation method

LDH containing Zn:Al molar ratio 3:1 was prepared by the co-precipitation method at a constant pH of 11. LDH/SDS precursor was synthesized with a 3:1 ratio of Zn(II) and Al(III) salt together with SDS as an intercalated anion. The synthesis procedure has been carried out in a $N_2$ atmosphere in order to avoid the formation of carbonate anions by atmospheric $CO_2$. The obtained material was separated by filtration and washed with distilled water. The material was dried at room temperature before further reaction and abbreviated as LDH/SDS. IR (KBr, cm$^{-1}$): 447, 675, 1047, 1202, 1384, 1471, 1620, 2852, 2873, 2927, 2962, 3487. Raman (cm$^{-1}$): 552, 582, 623, 830, 890, 1045, 1084, 2850, 2880, 2959, 3484. $^{13}$C CP MAS NMR (100.62 MHz, CDCl$_3$, ppm): δ=19.2 ($C_{12}$), 28.7 ($C_{11}$), 36.4 ($C_4$-$C_{10}$), 42.7 ($C_3$), 61.8 ($C_2$), 71.9 ($C_1$).

Surface Functionalization by APTES

LDH/SDS and CTAB were dried at 80° C. overnight to maintain an anhydrous condition. 30 ml of methylene dichloride was added to 1.75 gm of dried CTAB (0.16 M) under nitrogen atmosphere. 5 ml of APTES was added to the dried LDH precursor containing SDS. Then the CTAB solution containing methylene dichloride was added to the mixture of APTES and LDH/SDS. The whole mixture was allowed to react for about 48 hrs at room temperature. Finally the product was filtered, washed thoroughly with methylene dichloride. The product was dried at room temperature and abbreviated as LDH/APTES. IR (KBr, cm$^{-1}$): 447, 674, 840, 1384, 1628, 2840, 2922, 3352, 3392, 3481. Raman (cm$^{-1}$): 557, 1043, 1297, 1421, 2880, 2951, 3319, 3484. $^{13}$C CP MAS NMR (100.62 MHz, CDCl$_3$, ppm): δ=10.16 ($C_1$), 22.25 ($C_2$), 43.17 ($C_3$).

The FIG. 4 shows the schematic representation of SDS intercalated Zn:Al LDH. SDS intercalated LDH was allowed to react with CTAB in presence of APTES for the synthesis of APTES functionalised LDH.

The novelty of the present invention lies in the design and process for the preparation of APTES functionalised LDH (LDH/APTES) through simple ion exchange process and its use in catalytic amounts for C—C bond forming reactions (i.e. Aldol condensation, Knoevenagel condensation, Henry reaction, Michael addition). The consistent activity for several cycles in C—C bond formation reactions makes the process economical and possible for commercial realisation. Therefore, LDH/APTES is better alternative for of base catalyze reactions. Thus this invention offers the best techno-economic route for the synthesis of intermediates in the preparation of drugs, pharmaceuticals and fine chemicals. In the present invention the basal spacing has increased by the incorporation of sodium dodecyl sulfate (surfactant) followed by removal of surfactant by cetyl trimethylammonium bromide (CTAB) in dichloromethylene and subsequent attachment of aminopropyl triethoxy silane through covalent bonding to produce a sandwiched organic-inorganic heterostructure, which is used as a novel and reusable catalyst for base catalyzed reactions at room temperature.

Accordingly the present invention provides a novel process for preparation of aminopropyl triethoxysilane modified layered double hydroxide for C—C bond forming reactions which comprises, (a) slow addition of a mixed metal solution containing 2-3 g of $Zn(NO_3)_2.6H_2O$ and 1-2 g of $Al(NO_3).9H_2O$ in 65-75 ml of distilled water to an anionic solution containing 1-2 g of SDS in 60-70 ml of distilled water (b) pH of the whole solution was maintained at 7 by addition of 8 M NaOH solution (c) The total slurry solution was put to aging for 45-48 h at 65-70° C. (d) washing of the of the recovered catalyst after filtration and drying them overnight in open air (e) 4.5-5.5 ml of APTES was added to dried LDH precursor containing SDS and to this CTAB solution containing 25-30 ml of methylene dichloride was added and stirred for 40-48 h at room temperature (f) drying of the filtrate materials at room temperature.

In a feature of the present invention, zinc nitrate and aluminium nitrate are used as LDH precursor; SDS is used as an anionic surfactant, CTAB as cationic surfactant and APTES as organic precursor.

In another feature of the present invention, the precursors are taken in a definite proportion of $Zn(NO_3)_2:Al(NO_3)_3:SDS:CTAB:APTES=4:1:2:48.48:6.424$ to $2:1:4:80:12$.

In yet another embodiment of the present invention, the reactions are preferably performed at room temperature for a period of 0.5 to 48 h for base catalyzed C—C bond forming reactions (Aldol condensation, Knoevenagel condensation, Henry reaction, Michael addition).

In yet another embodiment of the present invention, the solvent selected is acetone, methanol, dichloromethane etc.

In still another embodiment of the present invention, LDH/APTES is prepared as exemplified and used in catalytic amounts for preparing Aldols/Knoevenagel/Henry/Michael adducts in a heterogeneous way as described in the examples.

The know-how for the synthesis of functionalised LDH and use in base catalyzed reactions is not available in the literature and it has been processed for the first time. The conditions prescribed in this invention are not specified by any other invention so far.

The following examples are given by way of illustration for the working of the invention in actual practice and therefore, should not be construed to limit the scope of the present invention.

Example 1

Preparation of $Zn^{2+}/Al^{3+}/NO_3^-$ LDH (Conditions: Zinc Nitrate=44.62 g, Aluminium Nitrate=18.75 g, Water=100 ml, pH 10)

The $Zn^{2+}/Al^{3+}/NO_3^-$ LDH with Zn/Al ratio 3:1 was prepared from $Zn(NO_3)_2.6H_2O$ (44.62 g, 0.15 mol) and $Al(NO_3)_3.9H_2O$ (18.75 g, 0.05 mol) which were dissolved in 100 ml of deionised water. The pH of the solution was adjusted to 10 by the addition of NaOH (2 M). The slurry was stirred for 2 h at 27° C. under nitrogen atmosphere and then filtered, washed thoroughly and dried under vacuum at 80° C.

Example 2

Preparation of $Zn^{2+}/Al^{3+}/SDS$ LDH (Conditions: Zinc Nitrate=2.97 g, Aluminium Nitrate=1.23 g, Water=140 ml, SDS=1.903 g, pH 7)

The Zn/Al/SDS LDH precursor was synthesized with 3:1 ratio of Zn(II) and Al(III) salt together with sodium dodecylsulfate (SDS) as an intercalated anions. The synthesis was carried out by a coprecipitation method by the slow addition of a mixed metal nitrate solution containing 0.01 mol (2.97 g) of $Zn(NO_3)_2.6H_2O$ and 0.0033 mol (1.23 g) of $Al(NO_3)_3.9H_2O$ in 70 ml of distilled and deionised water to an anionic solution containing 0.0066 mol (1.903 g) SDS in 70 ml of distilled water with constant stirring. During synthesis the pH of the solution was maintained at ~7.0 by the slow addition of 8 M NaOH solution. Total slurry solution was put to aging for 48 h at 65° C. The obtained material was filtered and washed by distilled water. The material was dried at room temperature for 12 hrs before further reaction.

Example 3

Preparation of Interlayer Surface Modified LDH by APTES (Conditions: Methylene Dichloride=30 ml, CTAB=1.75 g, APTES=5 ml)

Zn/Al-SDS LDH and CTAB were dried at 80° C. overnight to maintain an anhydrous condition. 30 ml of methylene dichloride was added to 1.75 gm of dried CTAB (0.16 M) under nitrogen atmosphere. 5 ml of APTES was added to dried LDH precursor containing SDS. Then the CTAB solution containing methylene dichloride was added to Zn/Al-SDS LDH precursors. The whole mixture was reacted for 48 hrs at 27° C. Then the products were thoroughly washed with methylene dichloride. Finally the product was filtered and dried at 27° C.

Figure 1:
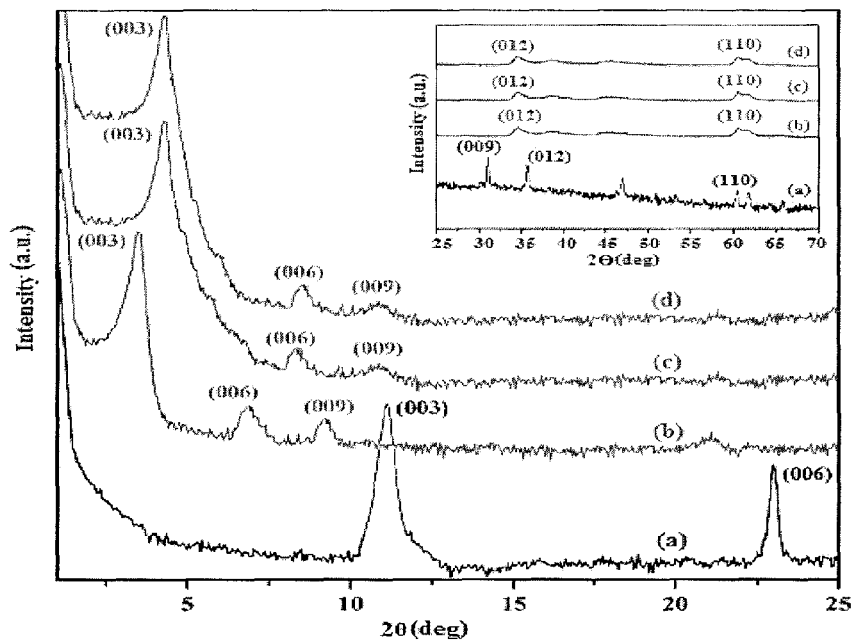
FIG. 1 Powder X-ray diffraction patterns of (a) ZnAl-LDH, (b) LDH/SDS and (c) LDH/APTES (d) Recovered catalyst.

The PXRD patterns of (a) ZnAl-LDH, (b) LDH/SDS, (c) LDH/APTES and (d) Recovered catalysts are presented in FIG. 1. The first basal diffraction maximum in ZnAl-LDH i.e. (003) at $2\theta=10.9°$ corresponds to a basal spacing of 8.32 Å. In case of SDS intercalated LDH, the position of (003) peak shifted to low $2\theta=3.32$ angle corresponding to the (003) Bragg reflection and give access to the interlayer distance $d_{003}$~26.9 Å, which is very close to the previously reported value in literature. The basal spacing of APTES/LDH found to be 23.2 Å is decreased by ~3.7 Å from that of SDS intercalated LDH. The reduction in basal spacing may suggest that dodecyl sulphate anion in the galleries are replaced by APTES moieties. The retention of characteristic peak (110) around $2\theta=60°$ after intercalation of the surfactant and organic moiety indicates that the structure of the layer has been retained.

Figure 2:
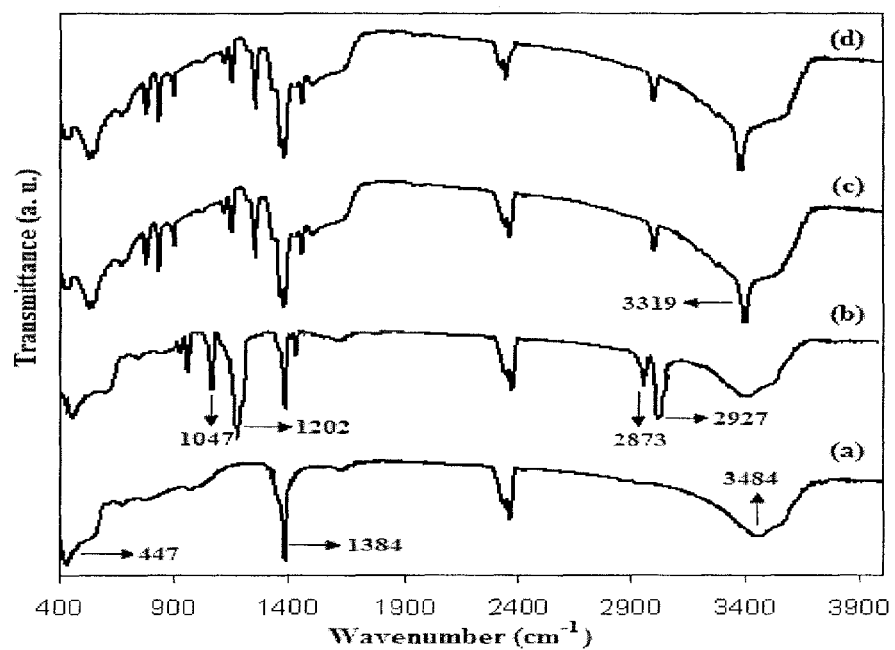
FIG. 2 FT-IR spectra of (a) LDH (b) LDH/SDS (c) LDH/APTES (d) Recovered catalyst.

FIG. 2. FT-IR spectra of (a) LDH (b) LDH/SDS (c) LDH/APTES (d) Recovered catalyst FTIR spectra of LDH, LDH/SDS, LDH/APTES, and recycled catalyst are shown in FIG. 2.

In case of LDH bands around 445 and 675 $cm^{-1}$ are due to Al—O and Zn—O lattice vibrations. Sharp band around 1384 $cm^{-1}$ is assigned to stretching vibration of interlayer $NO_3^-$. Broad bands in between 3300 and 3600 $cm^{-1}$ (as a result of H-bonding) is due to the v (OH) modes of the hydroxyl groups. The characteristic bands are detected for $SO_4^-$ group in LDH/SDS. Bands around 1047 and 1202 $cm^{-1}$ are due to asymmetric stretching of C—O and $SO_4^-$ bonds of surfactant. Typical C—H stretching modes for antisymmetric stretching of $CH_3$ and $CH_2$ at 2962 and 2927 $cm^{-1}$ and symmetric stretching of $CH_3$ and $CH_2$ at 2873 and 2852 $cm^{-1}$ respectively are observed. For APTES intercalated LDH, the intensities of the characteristic bands due to SDS molecules are generally weakened as compared with that of LDH/SDS. This is a clear indication of replacement of SDS molecules by APTES moiety and stabilized by $Br^-$ anions. In the spectra of LDH/APTES, the bands for $NH_2$ group of APTES molecule overlap with O—H stretching vibration of LDH to produce a merged spectrum in the range of 3300 to 3500 $cm^{-1}$. All the above results provide an indication of the presence of APTES in the LDH host.

Figure 3:
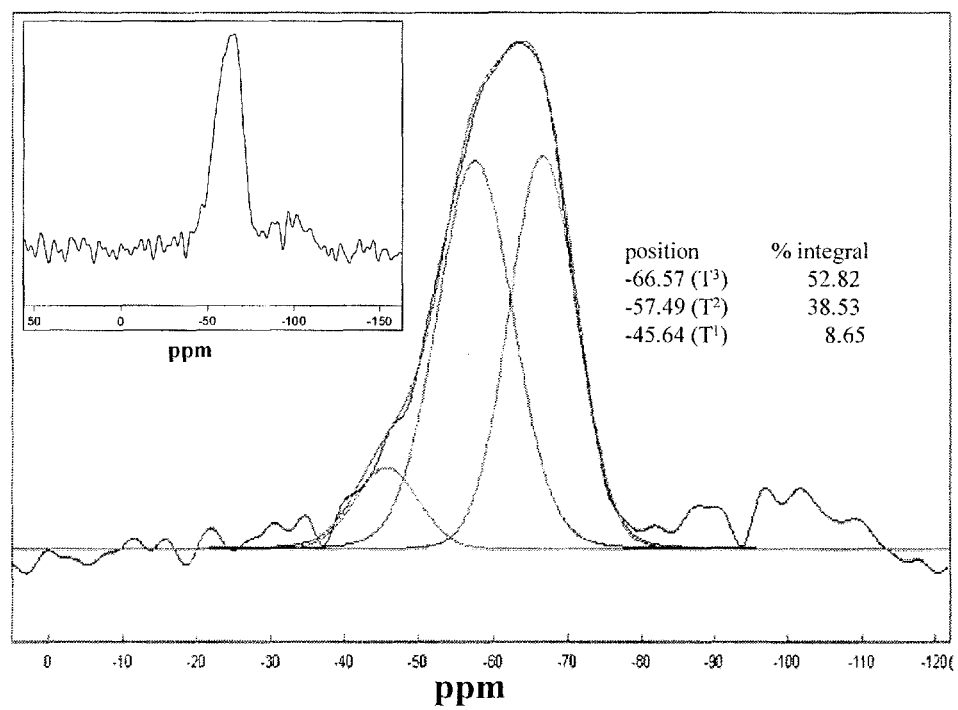
FIG. 3 $^{29}Si$ NMR spectra of LDH/APTES (Inserted) with deconvolution data for the relative population of M-O—Si bond.

$^{29}$Si CP MAS NMR spectra (FIG. 3)) provide significant information about the degree of functionalization and to evaluate the nature of the M-O—Si bond around Si atom. Peaks in the T region are contributed by Si atoms of the triethoxy silane and are denoted by T'" (n=0, 1, 2, 3), which are used to describe the extend of cross-linking depending on M-O—Si bond types. T$^3$ represents formation of three Si—O-M bonds, which indicates complete cross-linking in the hybrid materials, while T$^2$ represents formation of two Si—O-M bonds bearing one uncoordinated Si—OEt group. High intensity of T$^3$ peak reveals the high degree of condensation of the original triethoxy silane with LDH.

Example 4

Aldol Condensation Catalyzed by LDH/APTES (Conditions: Benzaldehyde=0.2 ml, Catalyst=0.05 g, Acetone=5 ml, Time=30 min, Reaction Performed at Room Temperature)

0.2 ml (2 mmol) of benzaldehyde, 0.05 g of catalyst, 5 ml of acetone were taken in a two-necked flask and the contents were stirred at 27° C. for 30 min. After completion of the reaction the catalyst was filtered off and washed with acetone. The product thus obtained (FIG. 1) was detected by Gas Chromatography to afford the corresponding aldol (i.e. 4-Phenyl-4-hydroxy-but-2-one) in 95% yield.

Example 5

Recycled Experiment Using LDH/APTES as Catalyst in Aldol Condensation (Conditions: Benzaldehyde=0.2 ml, Catalyst=0.05 g, Acetone=5 ml, Time=30 Min, Reaction Performed at Room Temperature)

A two-necked flask was charged with 0.2 ml (2 mmol) of benzaldehyde, 0.05 g of LDH/APTES, 5 ml of acetone and the contents were stirred at 27° C. for 30 min. After completion of the reaction, the catalyst was filtered, washed with dry acetone four times and dried in vacuum. The catalyst was thus recycled for 3 cycles with consistent activity. The product thus obtained was detected by Gas Chromatography to afford the corresponding aldol (4-Phenyl-4-hydroxy-but-2-one) in 93% yield.

Example 6

Aldol Condensation Catalyzed by LDH (Conditions: Benzaldehyde=0.2 ml, Catalyst=0.05 g, Acetone=5 ml, Time=30 min, Reaction Performed at Room Temperature)

0.2 ml (2 mmol) of benzaldehyde, 0.05 g of catalyst (LDH), 5 ml of acetone were taken in a two-necked flask and the contents were stirred at 27° C. for 30 min. After completion of the reaction the catalyst was filtered off and washed with acetone. The product (FIG. 1) thus obtained was detected by Gas Chromatography to afford the corresponding aldol (4-Phenyl-4-hydroxy-but-2-one) in 84% yield.

Example 7

Knoevenagel Condensation Catalyzed by LDH/APTES (Conditions: Benzaldehyde=0.2 ml, Catalyst=0.05 g, DMF=5 ml, Ethyl Cyanoacetate=0.226 ml, Time=90 Min, Reaction Performed at Room Temperature)

Benzaldehyde (2 mmol, 0.2 ml) and 0.05 g of LDH/APTES were stirred in 5 ml of dimethylformamide for 5 min. Then the active methylene compound i.e. ethyl cyanoacetate (2 mmol, 0.226 ml) was added and stirring was continued till 90 min at 27° C. The catalyst was filtered and the product was extracted with ethyl acetate, dried over anhydrous sodium sulfate. The final product (FIG. 2) was confirmed by Gas chromatography to afford the product (3-phenyl-2-propanoyl-prop-2-ene-nitrile) in 98% yield.

Example 8

Recycled Experiment Using LDH/APTES as Catalyst in Knoevenagel Condensation (Conditions: Benzaldehyde=0.2 ml, Catalyst=0.05 g, DMF=5 ml, Ethyl Cyanoacetate=0.226 ml, Time=90 min, Reaction Performed at Room Temperature)

Benzaldehyde (2 mmol, 0.2 ml) and 0.05 g of LDH/APTES were stirred in 5 ml of dimethylformamide for 5 min. Then the active methylene compound i.e. ethyl cyanoacetate (2 mmol, 0.226 ml) was added and stirring was continued till 90 min at 27° C. After completion of the reaction, the catalyst was filtered, washed with dry acetone four times and dried in vacuum. The catalyst was thus recycled for 3 cycles with consistent activity. The product (FIG. 2) thus obtained was detected by Gas Chromatography to afford the product (3-phenyl-2-propanoyl-prop-2-ene-nitrile) in 95% yield.

Example 9

Knoevenagel Condensation Catalyzed by LDH (Conditions: Benzaldehyde=0.2 ml, Catalyst=0.05 g, DMF=5 ml, Ethyl Cyanoacetate=0.226 ml, Time=90 Min, Reaction Performed at Room Temperature)

Benzaldehyde (2 mmol, 0.2 ml) and 0.05 g of LDH were stirred in 5 ml of dimethylformamide for 5 min. Then the active methylene compound i.e. ethyl cyanoacetate (2 mmol, 0.226 ml) was added and stirring was continued till 90 min at 27° C. The catalyst was filtered and the product was extracted with ethyl acetate, dried over anhydrous sodium sulfate. The final product (FIG. 2) was confirmed by Gas chromatography to afford the corresponding product (3-phenyl-2-propanoyl-prop-2-ene-nitrile) in 88% yield.

Example 10

Henry Reaction Catalyzed by LDH/APTES (Conditions: Nitromethane=0.54 ml, Benzaldehyde=0.2 ml, Catalyst=0.03 g, Time=60 min, Reaction Performed at Room Temperature)

To a mixture of nitromethane (10 mmol, 0.54 ml) and benzaldehyde (2 mmol, 0.2 ml), 0.03 g of catalyst was added and stirred for 60 min at 27° C. The catalyst was filtered and washed with dichloromethane. The final product (FIG. 3) was confirmed by Gas chromatography to afford the corresponding product (2-hyroxy-3-phenyl-1-nitropropane) in 97% yield.

Example 11

Recycled Experiment Using LDH/APTES as Catalyst in Henry Reaction (Conditions: Nitromethane=0.54 ml, Benzaldehyde=0.2 ml, Catalyst=0.03 g, Time=60 Min, Reaction Performed at Room Temperature)

To a mixture of nitromethane (10 mmol, 0.54 ml) and benzaldehyde (2 mmol, 0.2 ml), 0.03 g of catalyst was added and stirred for 60 min at 27° C. The catalyst was filtered and washed with dichloromethane. The catalyst was thus recycled for 3 cycles with consistent activity. The product (FIG. 3) thus obtained was detected by Gas Chromatography to afford the product (2-hyroxy-3-phenyl-1-nitropropane) in 93% yield

Example 12

Henry Reaction Catalyzed by LDH (Conditions: Nitromethane=0.54 ml, Benzaldehyde=0.2 ml, Catalyst=0.03 g, Time=60 min, Reaction Performed at Room Temperature)

To a mixture of nitromethane (10 mmol, 0.54 ml) and benzaldehyde (2 mmol, 0.2 ml), 0.03 g of catalyst (LDH) was added and stirred for 60 min at 27° C. The final product (FIG. 3) was confirmed by Gas chromatography to afford the product (2-hyroxy-3-phenyl-1-nitropropane) in 89% yield.

Example 13

Michael Addition Catalyzed by LDH/APTES (Conditions: Ethyl Ester of Cinnamic Acid=0.33 ml, Catalyst=0.05 g, Methanol=10 ml, Diethyl Malonate=0.3 ml Time=24 h, Reaction Performed at Room Temperature)

Figure 4:
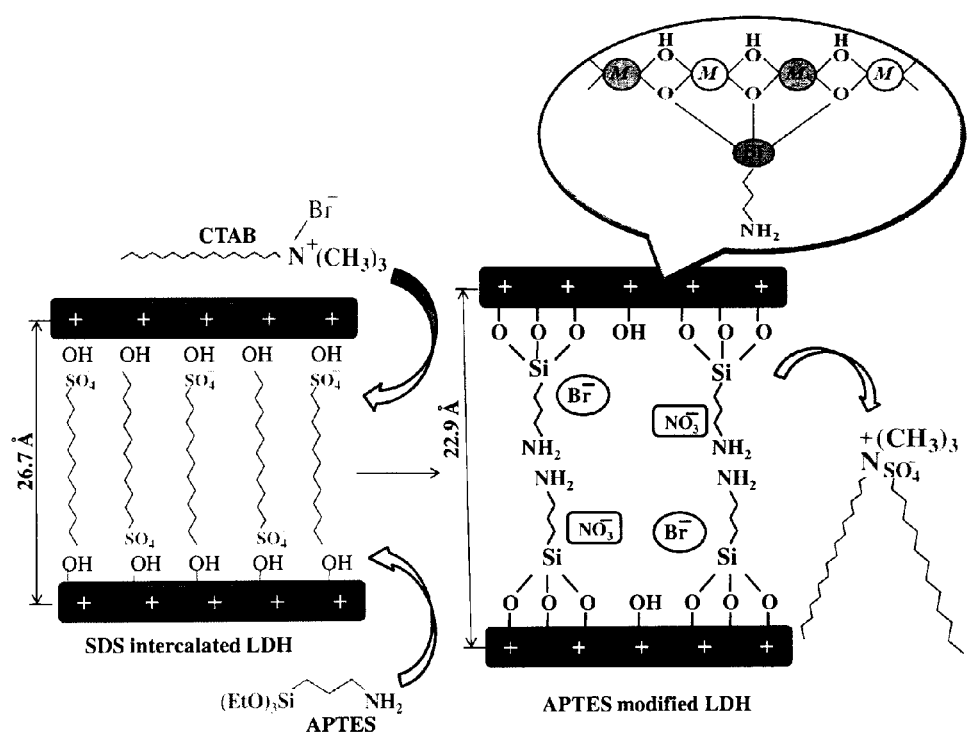
FIG. 4 shows the schematic representation of SDS intercalated Zn:Al LDH.

Acceptor specis i.e. ethyl ester of cinnamic acid (2 mmol, 0.33 ml) and 0.05 g of catalyst were stirred in 10 ml of methanol for 5 min., then donor specis i.e. diethyl malonate (2 mmol, 0.3 ml) was added and stirred for 24 h at 27° C. The product (FIG. 4) thus obtained was detected by Gas Chromatography to afford the corresponding product (2-propanoyl-3-phenyl-1,5-diethyl pentanedioate) in 98% yield.

Example 14

Recycled Experiment Using LDH/APTES as Catalyst in Michael Addition (Conditions: Ethyl Ester of Cinnamic Acid=0.33 Ml, Catalyst=0.05 g, Methanol=10 Ml, Diethyl Malonate=0.3 Ml Time=24 h, Reaction Performed at Room Temperature)

Ethyl ester of cinnamic acid (2 mmol, 0.33 ml) and 0.05 g of catalyst were stirred in 10 ml of methanol for 5 min., and then diethyl malonate (2 mmol, 0.3 ml) was added and stirred for 24 h at 27° C. After completion of the reaction, the catalyst was filtered, washed with dry acetone four times and dried in vacuum. The catalyst was thus recycled for 3 cycles with consistent activity. The product (FIG. 4) thus obtained was detected by Gas Chromatography to afford the product (2-propanoyl-3-phenyl-1,5-diethyl pentanedioate) yield 95%.

Example 15

Michael Addition Catalyzed by LDH (Conditions: Ethyl Ester of Cinnamic Acid=0.33 Ml, Catalyst=0.05 g, Methanol=10 Ml, Diethyl Malonate=0.3 Ml Time=48 h, Reaction Performed at 27° C.)

Acceptor specis i.e. ethyl ester of cinnamic acid (2 mmol, 0.33 ml) and 0.05 g of catalyst were stirred in 10 ml of methanol for 5 min., and then donor specis i.e. diethyl malonate (2 mmol, 0.3 ml) was added and stirred for 48 h at 27° C. The product (FIG. 4) thus obtained was detected by Gas Chromatography to afford the product (2-propanoyl-3-phenyl-1,5-diethyl pentanedioate) yield 85%.

The main advantages of the present invention are:
1. A novel process for the covalent attachment of aminopropyl triethoxysilane to LDH is presented which comprises of easy steps.
2. The present process dispenses the use of soluble bases or amine instead a heterogeneous reusable LDH-APTES is used, the catalytic reaction process is accomplished in a short time at room temperature to afford high productivity.
3. The developed process is simple, economical and environmental friendly since there is no disposal problem.
4. The catalyst is subjected to many recyclability tests, which displayed consistent activity.

We claim:

1. A modified layered double hydroxide (LDH) catalyst wherein the catalyst comprising: $Zn(OH)_2$, $Al(OH)_3$ and APTES ranging between 76-70%, 21-24% and 3-6%, respectively wherein the basal spacing ($d_{003}$) peak is at 23.2 Å and Al—O and Zn—O lattice vibrations is around 445 and 675 $cm^{-1}$ in LDH.

2. A method for C—C bond formation reaction comprising the step of catalysis by the modified layered double hydroxide (LDH) of claim 1.

3. The method of claim 2, wherein the C—C bond forming reactions is selected from a group consisting of aldol/$\alpha,\beta$-unsaturated ester/$\beta$-nitroalkanols/Michael addition product, aldol condensation, Knoevenagel condensation, and Henry reaction.

4. The method of claim 2, wherein the reaction is performed at a temperature in the range of 20° C. to 35° C. in the presence of the modified layered double hydroxide (LDH).

5. The method of claim 2, wherein the reaction is performed for a period of 0.5 to 48 hrs in the presence of the modified layered double hydroxide (LDH).

6. The method as claimed in claim 4, wherein yield of the products obtained is in the range of 80-98%.

7. A process for preparation of modified layered double hydroxide as claimed in claim 1, said process comprising the steps of:
(a) preparing a mixed solution of $Zn(NO_3)_2.6H_2O$ and $Al(NO_3).9H_2O$ in water in a ratio ranging between 4:1 to 2:1 respectively at a pH of 10 by addition of NaOH,
(b) adding slowly the mixed solution of step (a) to an anionic solution of sodium dodecyl sulfate (SDS) in water,
(c) adding NaOH solution to the above said mixture of step (b) to maintain pH of the whole solution at 7 to obtain a slurry;
(d) aging the slurry obtained in step (c),
(e) filtering the product thus obtained in step (d) and washing with water, followed by drying to obtain an LDH precursor containing SDS, (f) adding aminopropyl triethoxysilane (APTES) to the LDH precursor containing SDS of step (e) followed by addition of cetyl trimethylammonium bromide (CTAB) in a solvent and kept/set aside the whole mixture for reaction, (g) washing a product thus obtained in step (f), filtering and drying to obtain the modified layered double hydroxide (LDH).

8. The process as claimed in claim 7, wherein a ratio of Zn:Al:SDS in step (b) is in the range of 4:1:2 to 2:1:4, respectively.

9. The process as claimed in claim 7, wherein a ratio of $Zn(NO_3)_2$:$Al(NO_3)_3$:SDS:CTAB:APTES is in the range of 4:1:2:48.48:6.424 to 2:1:4:80:12.

10. The process as claimed in claim 7, wherein the slurry in step (d) is aged for 45-48 hrs.

11. The process as claimed in claim 7, wherein the slurry in step (d) is aged at a temperature in the range of 65° C. to 70° C.

12. The process as claimed in claim 7, wherein the whole reaction mixture in step (f) is reacted for 40-48 hrs.

13. The process as claimed in claim 7, wherein the whole reaction mixture in step (f) is reacted at a temperature in the range of 20-35° C.

14. The process as claimed in claim 7, wherein the solvent used in step (f) is selected from group consisting of dichloromethylene, chloroform, ethanol, and methanol.

15. The process as claimed in claim 7, wherein washing of the product in step (g) is done with dichloromethane.

16. The process as claimed in claim 7, wherein drying in step (g) is carried out at a temperature range of 20° C.-35° C.

17. The method as claimed in claim 5, wherein yield of the products obtained is in the range of 80-98%.

* * * * *